(12) United States Patent
McLeod

(10) Patent No.: US 8,480,758 B2
(45) Date of Patent: Jul. 9, 2013

(54) PROSTHESIS FIXATION WITH MECHANICALLY COMPACTED BIOCOMPATIBLE GRANULES

(75) Inventors: Allan Gordon McLeod, Hereford (GB); Daniel John Donald McLeod, legal representative, London (GB)

(73) Assignee: Fondel Finance, B.V., Rotterdam (NL)

( * ) Notice: Subject to any disclaimer, the term of this patent is extended or adjusted under 35 U.S.C. 154(b) by 1925 days.

(21) Appl. No.: 10/979,797

(22) Filed: Oct. 29, 2004

(65) Prior Publication Data

US 2005/0165494 A1   Jul. 28, 2005

Related U.S. Application Data

(63) Continuation of application No. PCT/NL03/00315, filed on Apr. 29, 2003.

(30) Foreign Application Priority Data

Apr. 29, 2002 (NL) .................................... 1020501

(51) Int. Cl.
*A61F 2/02* (2006.01)
*A61B 17/60* (2006.01)

(52) U.S. Cl.
USPC .......................................... 623/23.73; 606/99

(58) Field of Classification Search
USPC ........ 606/86 R, 92–94, 99; 623/23.61–23.63, 623/23.73
See application file for complete search history.

(56) References Cited

U.S. PATENT DOCUMENTS

| | | | | |
|---|---|---|---|---|
| 5,015,256 A | * | 5/1991 | Bruce et al. | 128/898 |
| 5,389,107 A | | 2/1995 | Nassar et al. | 623/23 |
| 5,735,855 A | * | 4/1998 | Bradley | 606/86 R |
| 6,045,555 A | * | 4/2000 | Smith et al. | 606/80 |
| 6,270,502 B1 | * | 8/2001 | Stulberg | 606/86 R |

FOREIGN PATENT DOCUMENTS

| | | |
|---|---|---|
| DE | 2 305 441 | 8/1974 |
| DE | 43 27 054 | 4/1995 |
| EP | 0 501 595 | 9/1992 |
| EP | 0 792 628 | 9/1997 |
| EP | 0 950 389 | 10/1999 |
| FR | 2 483 218 | 12/1981 |
| FR | 2 779 941 | 12/1999 |
| WO | WO 00/13615 | 3/2000 |

OTHER PUBLICATIONS

Cotton, F. Albert, et al., "Anorganische Chemie," 1970, pp. 749-754, Interscience Publishers.
English abstract of DE 43 27 054, Jan. 14, 2005.
English abstract of EP 0 792 628, Jan. 14, 2005.
English abstract of EP 0 950 389, Jan. 14, 2005.
English abstract of FR 2 483 218, 2005.
English abstract of FR 2 779 941, Jan. 14, 2005.

* cited by examiner

*Primary Examiner* — Anu Ramana
(74) *Attorney, Agent, or Firm* — Banner & Witcoff, Ltd.

(57) ABSTRACT

An assembly for fixating a prosthesis in body tissue such as bone of a mammal, comprising a mechanical compacting device and a mass comprising at least granules of a biocompatible material having a sponge-like structure, wherein the mechanical compacting device is designed for compacting the granules during use by insertion of the device in a hole in bone and subsequently inducing relative movement of at least a first part of the compacting device relative to a second part thereof, such that the volume of at least one space between at least part of an outer surface of the device and the adjacent inner surface of said hole is reduced.

35 Claims, 7 Drawing Sheets

PROSTHESIS FIXATION WITH MECHANICALLY COMPACTED BIOCOMPATIBLE GRANULES

RELATED APPLICATIONS

Figure 1:
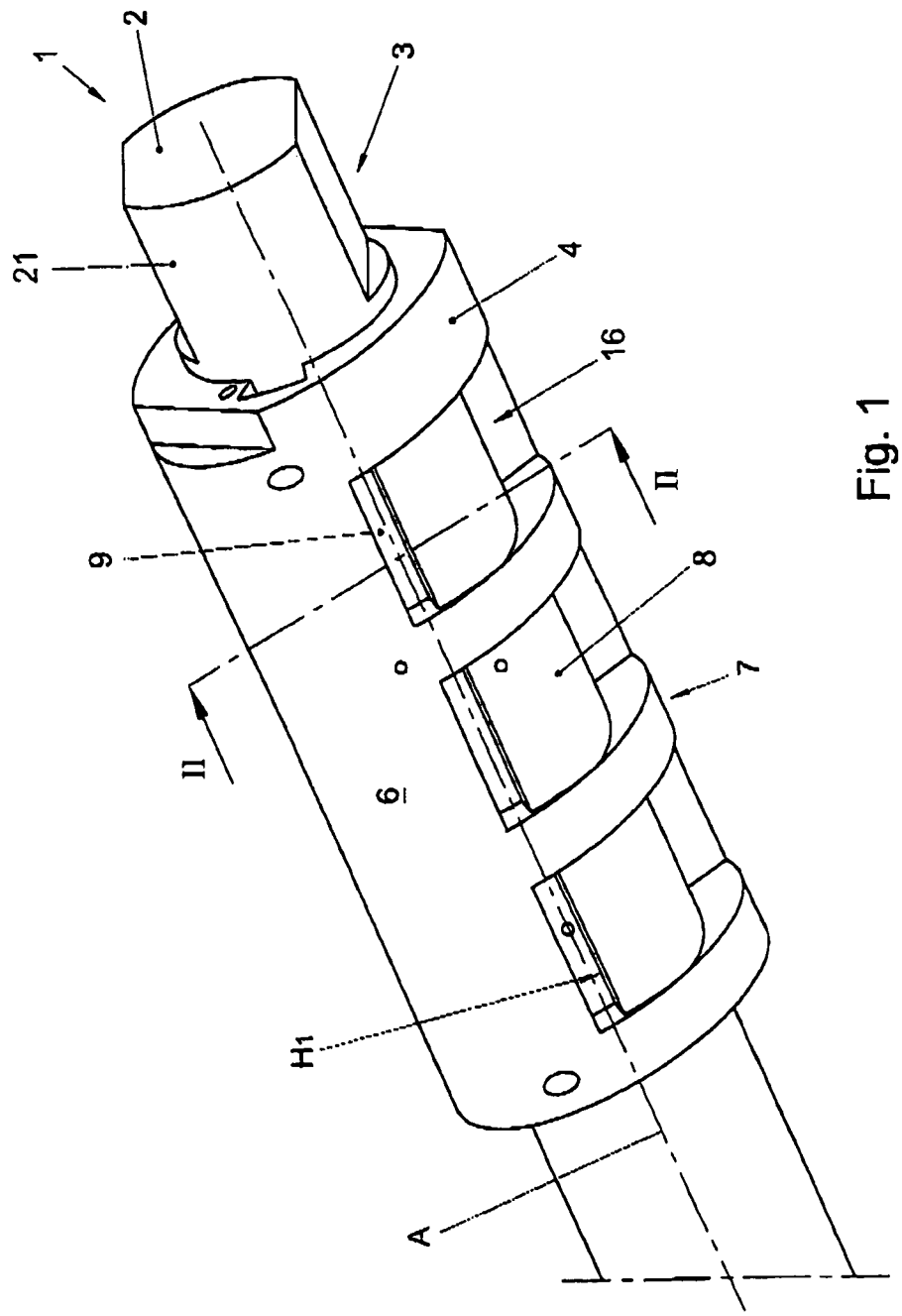

This application is a continuation of PCT application no. PCT/NL03/00315, designating the United States and filed Apr. 29, 2003; which claims the benefit of the filing date of Dutch application no. NL 1020501, filed Apr. 29, 2002; both of which are hereby incorporated herein by reference.

The invention relates to an assembly for fixating a prosthesis in body tissue such as bone. The invention further relates to a prosthesis and a method for fixating such prosthesis, as well as to the use of biocompatible granules in fixating a prosthesis.

In fixating a prosthesis in bone various methods are known from the state of the art, such as use of cement, means for fixating based on memory metal or use of other mechanical fixating means such as pins, screws, plates and the like.

WO00/13615 discloses a method for fixating a prosthesis in bone by using an implant comprising a pouch filled with a batch of a mixture of porous granules of tissue compatible material and disintegrated tissue-compatible biological material such as bone meal, to which a further tissue-biocompatible component has been added which allows modelling or moulding of the mixture within the pouch. The pouch is vibrated in order to obtain sufficient compacting of the mixture, prior to use. The pouch is fitted into a cavity such as an acetabulum cavity for a hip prosthesis, whereupon a plastic acetabulum cup, coated with titanium is press fitted into said cavity, onto said pouch. In this method ingrowth and outgrowth of tissue material through the pouch occurs, resulting in a biological fixture of the cup to the bone of the pelvis.

This known method has the disadvantage that the compacting of the pouch will be uniform, due to the vibration used for compacting. This means that in use the compactness of the mixture between the bone and the prosthesis cannot be influenced, which is undesirable. Moreover, in this known method the prosthesis cannot immediately be loaded after positioning.

From practice it is furthermore known to fixate a prosthesis such as a hip prosthesis in a femur, by drilling a hole in the femur, partly filling the hole with a mixture of titanium granules, biological tissue such as bone tissue and a nutrient and subsequently introducing the stem of the prosthesis into the hole, after which the granule mixture is vibrated by, for example, high or low frequency vibration, simultaneously pressing the stem down into the hole. The granule mixture is then forced upward along the stem and simultaneously compacted between the inner wall of the hole and the outer surface of the stem. This known method has the disadvantage the vibration has to be accomplished when the stem is in the femur, simultaneously forcing down the stem, whereas the compacting cannot be regulated along the length of the stem.

The present invention has as a main objective to provide an assembly for fixating a prosthesis in bone, preventing at least a number of the disadvantages of the known methods and assemblies, maintaining most of the advantages thereof.

The present invention more specifically has the objective to provide such assembly which allows regulation of the compacting of a mixture comprising porous granules along an outer surface of part of a prosthesis, so as to obtain a desired distribution of said compacting along said part of said prosthesis.

A further objective of the present invention is to provide for a prosthesis which can be fixated in bone without the necessity of vibrating, especially the bone, when placing said prosthesis.

A still further object of the present invention is to provide for a prosthesis or assembly, which enables easy positioning and fixation, inducing bone growth for fixation.

Furthermore, the present invention has as an objective to provide a method for fixating a prosthesis in bone in a secure and easy manner.

Moreover the present invention has as an objective to provide for use of biocompatible granular sponge like material in fixation of prosthesis in bone, especially by using chemically treated titanium or titanium blends.

These and further object are obtained by an assembly, prosthesis, method and use according to the present invention.

In an assembly according to the present invention as defined in claim 1, mechanical compacting means are provided for compacting the mass comprising granules at least partly when the prosthesis is introduced into an aperture such as a bore in bone. The mechanical means are designed for compacting the granules within said hole, against the inner wall of said aperture and/or within said compacting means, whereas bone and tissue can grow at least into said granules, from the wall of said aperture.

In an assembly according to the present invention, the further advantage is obtained that the prosthesis can immediately be loaded, whereas the force exerted on the wall of the bone, by the prosthesis, especially by the compacting means and granules can be closely controlled. This is very advantageous since too high pressures might cause bone resorption. With an assembly according to the present invention excellent growth conditions can repeatedly be obtained.

This mass comprising granules preferably comprises granules obtained by a reaction with titanium tetrachloride.

In a preferred embodiment in an assembly according to the present invention the compacting means are designed for compacting the mass comprising granules to different compact rates along a longitudinal extent of at least part of the prosthesis or over a surface of said part of the prosthesis. For example around a neck part of a prosthesis the compacting rate can be higher than at a distance from the neck, such that the compacting rate near the opening of the aperture/bore into which the prosthesis is introduced is higher than further down into the bore. Tests show that this may be advantageous, for example for inducing micro movement within the mass, further inducing tissue growth into the mass, more specifically into the granules.

The mass may comprise granules of different hardness and/or sizes, whereas the distribution of the different granules may be readily chosen, depending on desired compacting rate and extent and rate of tissue growth into said mass.

The compacting means may usefully be designed for compacting the mass comprising granules by rotation of different parts relative to each other. In such embodiment the prosthesis, i.e. a part of a fixing means such as part of a stem and the compacting means are inserted into an opening such as a bore in bone, whereupon the rotation is initiated, compacting the mass. This has the advantage that the prosthesis or at least the part introduced into the opening can be positioned in a desired position before compacting. The compacting therefore has relatively little or no influence on the position. In an alternative embodiment, the compacting means can be designed for compacting by a translation or a combined translation and rotation. For example by placing a stem of a prosthesis in an opening in bone, resting on a bottom of the opening, whereupon part of the compacting means is forced along the stem, up or downward in the opening, thereby compacting the mass. Such movement can easily be induced. The mass comprising the granules can be adhered to part of the prosthesis, for example by using bio compatible means such as collagens, starch, glue or the like. The same means can be used for interconnecting the granules and possibly further contents of the mass. In an alternative embodiment the mass can be enclosed within a casing extending around at least part of fixation means of said prosthesis, which casing is susceptible to growth of body tissue such as bone tissue through the casing, into or from bone surrounding said part. The casing may be rigid or flexible and may be biocompatible and/or bio-resorbable. Combinations are obviously also possible.

The present invention further relates to a prosthesis comprising a fixation part such as a stem, wherein on at least a part of said fixation part compacting means are provided and a mass comprising at least granules of a biocompatible material having a sponge-like structure, enclosed within said compacting means, such that during use the compacting means are operable when said fixation means are inserted into a bore in bone and bone growth is enabled through at least part of the compacting means, from the wall of said bore in said bone as far as into said granules.

Such prosthesis has the advantage that it can be easily fixated in bone and induces bone growth for relative quick fixation by bone growth into a mass surrounding at least part of fixation means of said prosthesis.

A prosthesis according to the present invention has the advantage that the mass comprising granular material can be fixed to the prostheses and/or compacting means prior to use, prior to introduction into bone.

The present invention relates to a method for fixation of a prosthesis in bone, comprising the steps of: providing a hole in said bone; introducing a compacting device and a fixation element such as a stem of a prosthesis into said hole; introducing a mass comprising at least granules of a biocompatible, sponge-like material into at least one space, in said compacting device and/or between at least part of said compacting device and an inner wall of said hole; and moving a first part of the compacting device relative to a second part of said device, thereby reducing the volume of said at least one space and compacting at least part of the mass within said compacting device and/or between the compacting device and said inner wall part.

Such method has the advantage that a prosthesis can be easily positioned and fixated in an opening such as a bore in bone, compacting a mass surrounding part of the prosthesis, inducing and/or enhancing growth of body tissue such as bone into the mass and/or from this mass into surrounding bone or other body tissue. Such growth leads to a better fixation. Since the compacting is obtained using mechanical means, the rate of compacting can be readily and securely controlled and varied, while undesired vibrations can be avoided, which is favourable for the patient. Furthermore the microstructure of the granules in the mass can be better maintained, especially said porosity.

The present invention further relates to a method for preparation of a prosthesis for fixation in an opening wherein the prosthesis is provided with compacting means which enclose at least one space, into which at least one space a mass is introduced, said mass comprising at least granules of a biocompatible material having a sponge-like structure and, preferably, biological material compatible with the bone into which said prosthesis is to be positioned, said compacting means being arranged for compacting said mass around at least part of fixation means of said prosthesis.

By preparing a prosthesis with a mass comprising biocompatible, granules having a sponge like structure, especially microstructure and compacting means for mechanically compacting the mass, the prosthesis is ready for implantation and fixation.

The granules used within the present invention are preferably made of or at least comprise titanium or titanium alloy and/or reaction products of titanium tetrachloride resulting in a desired sponge-like structure. Such granules have proven to be preferable over granules made by forcing gas through molten titanium, for better ingrowth of body tissue, especially bone, and more controlled porosity.

Further advantageous embodiments of an assembly, prosthesis and method according to the present invention are given in the further subclaims.

Figure 2:
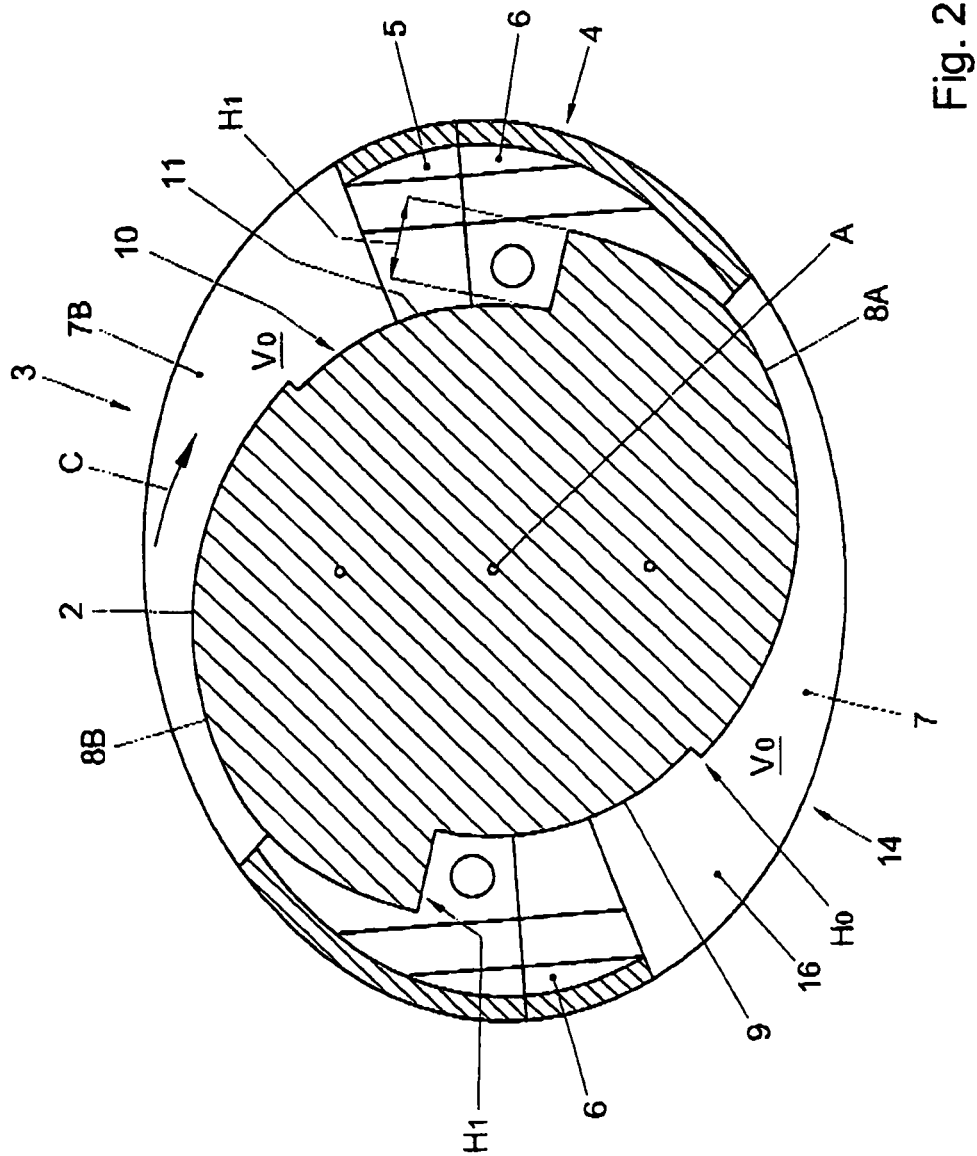
Figure 3:
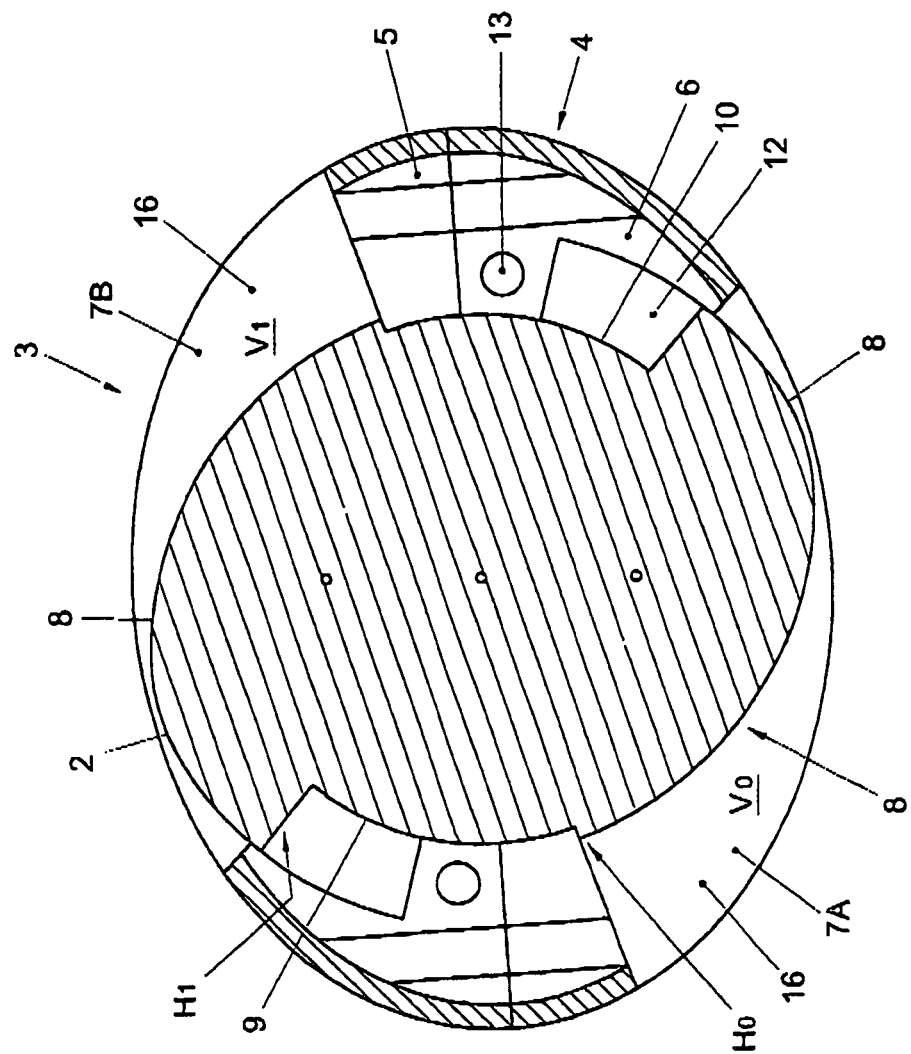
Figure 4:
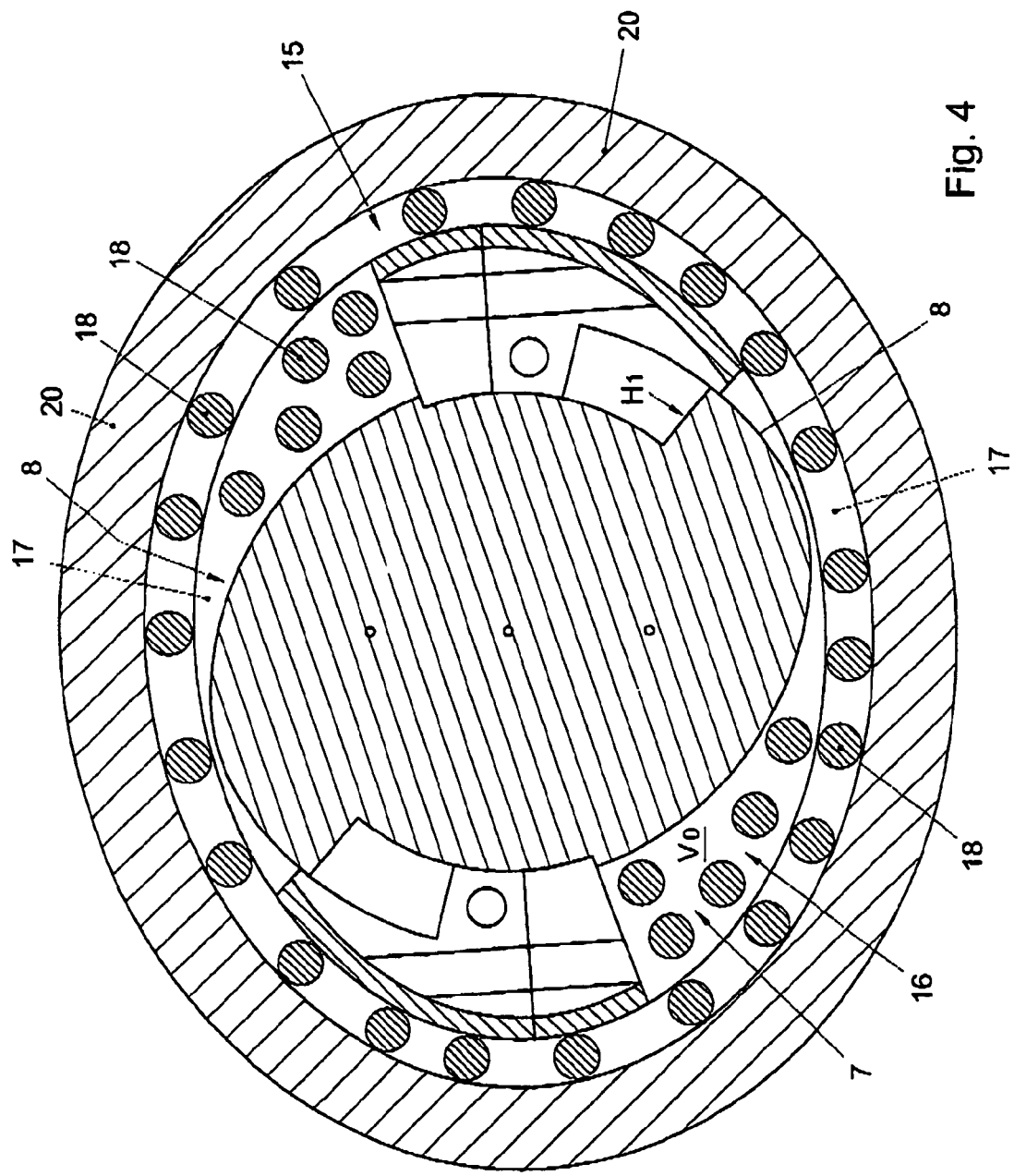
Figure 5:
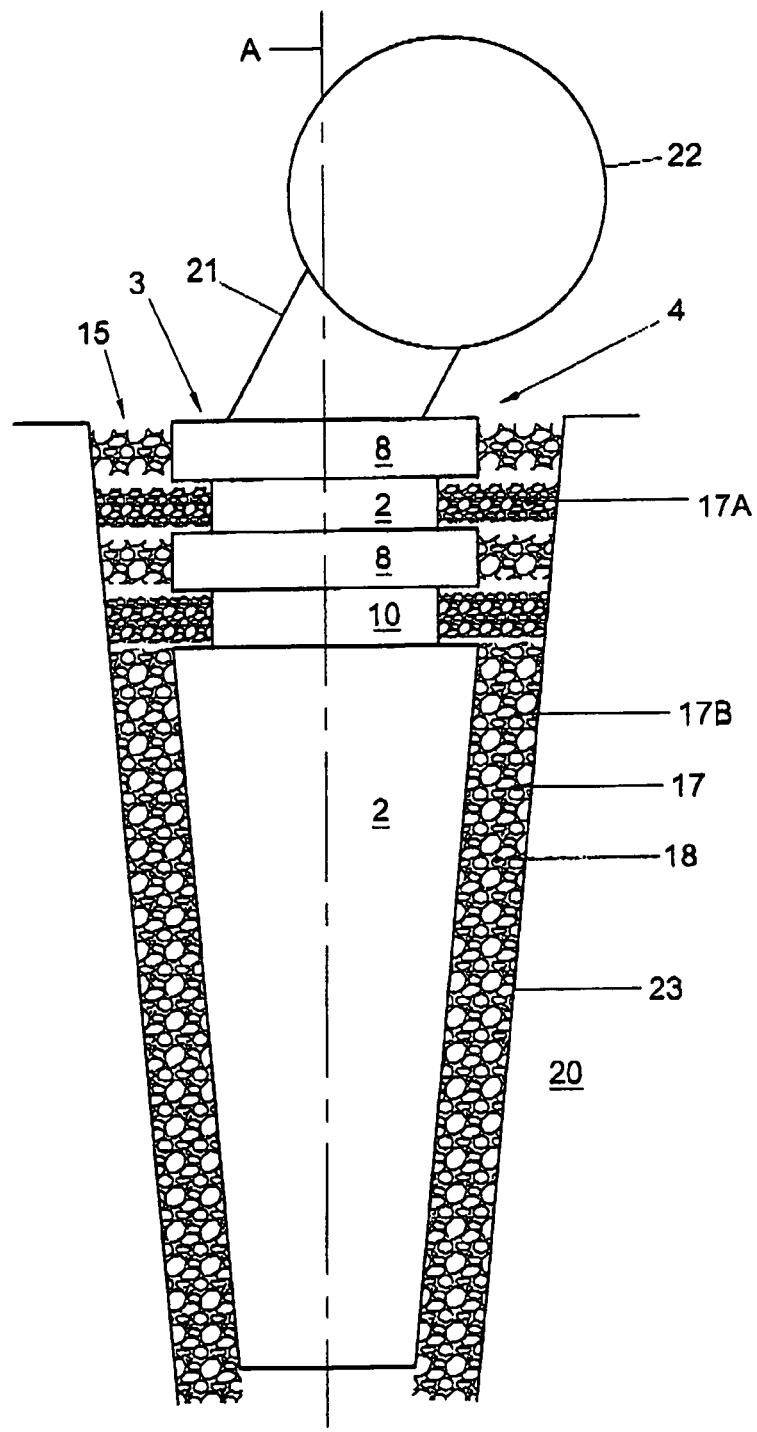
Figure 6:
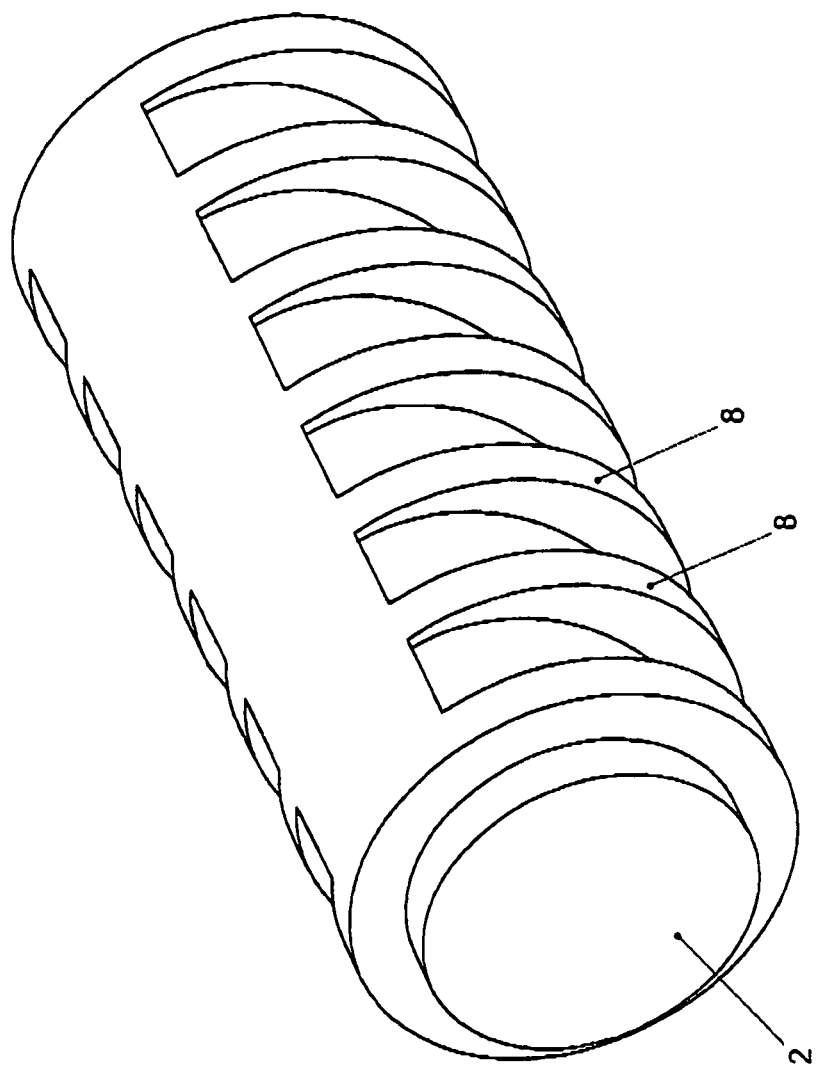
Figure 7:
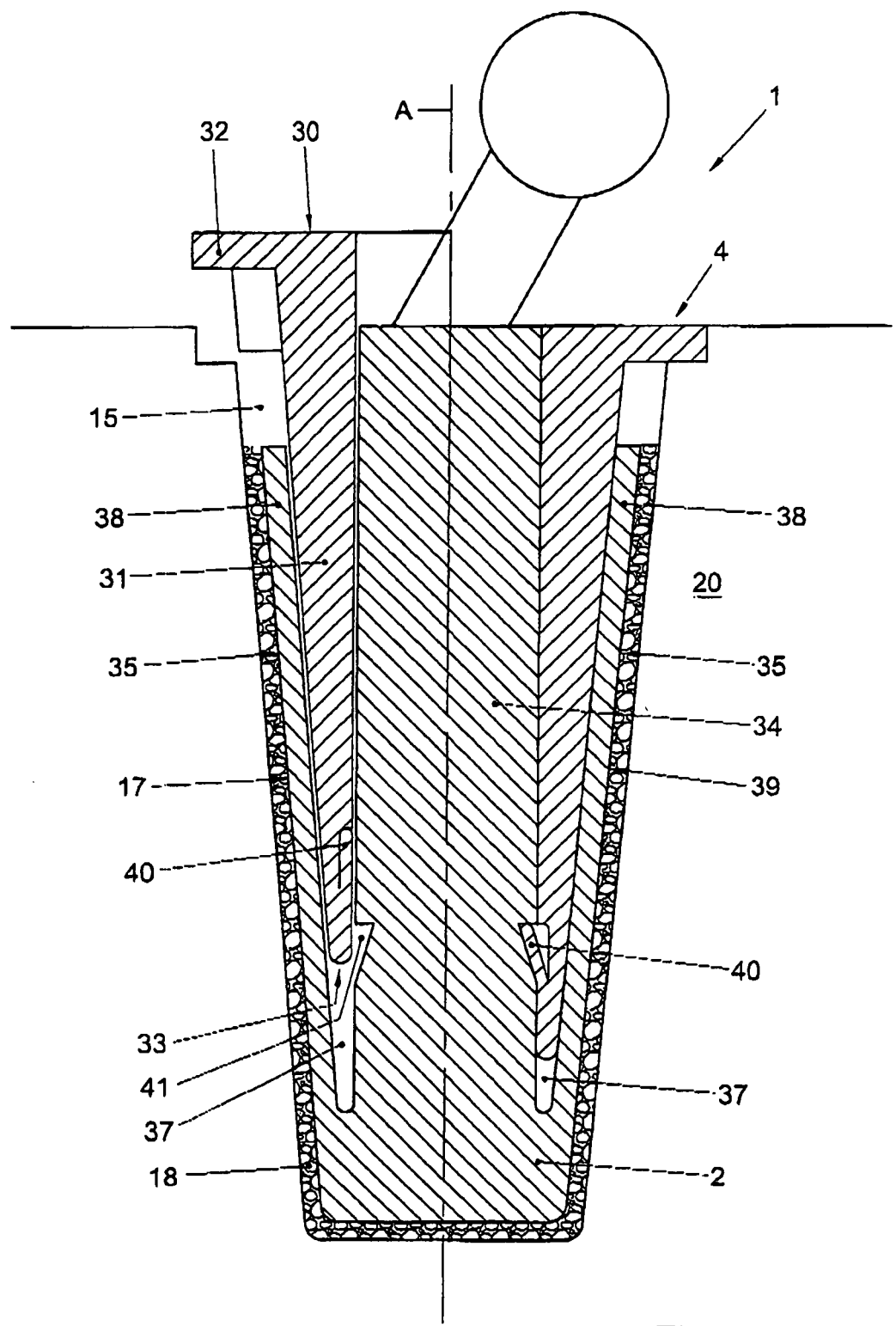

For a better understanding of the present invention different embodiments are presented in the drawings, by way of example only. In the drawings:

FIG. 1 schematically shows, in perspective view, part of an assembly of a prosthesis with compacting means according to the present invention;

FIG. 2 schematically shows, in cross section, the prosthesis according to FIG. 1, in a so-called closed position, ready for insertion into a hole in bone;

FIG. 3 schematically shows the same cross-section of FIG. 2, in a so-called open position, in which fixation can occur;

FIG. 4 schematically shows the prosthesis in cross section according to FIGS. 2 and 3, in the open position, inserted in bone;

FIG. 5 schematically shows an example of a prosthesis according to the present invention, in side view, inserted in bone;

FIG. 6 schematically shows part of a compacting means, in perspective view, for use in an assembly according to the present invention; and FIG. 7 schematically shows an example of a prosthesis according to the present invention in a further embodiment.

In these drawings identical or corresponding parts have identical or corresponding reference numerals.

In the examples shown in the drawing a hip prosthesis is shown. It will be clear that similar compacting means can be used for other prostheses, especially prostheses for other joints.

FIG. 1 schematically shows, in perspective view, a part of an assembly 1 according to the present invention, more specifically part of a stem 2 of a prosthesis 3, partly surrounded by compacting means 4. FIG. 2 shows a cross section perpendicular to the longitudinal axis A of the stem 2 along line II. This FIG. 2 shows the stem 2 and a casing 5 of the compacting means 4, which casing comprising two spines 6 opposite each other, extending in a longitudinal direction along part of the stem 2, these spines being connected by a number of bridges 7 surrounding the stem 2. FIG. 6 shows in a perspective view part of the stem 2, which is to be surrounded by the casing 5. FIG. 6 clearly shows a series of cams 8 on two opposite sides of the stem 2, each cam 8 having an increasing radial height, increasing from a height $H_0$ above a central circular cross section 9 of the stem 2 two a height $H_1$. As can be seen from FIG. 2, the cams 8 are positioned diametrically opposite each other, such that part of the cylindrical surface 10 of the stem 2 lies free between the lowest end $H_0$ of a first cam 8A and the adjacent high end of opposite cam 8B. The spines 6 lie, between two bridges 7, in a snugly fitting manner against the outer surface 10 with a counter surface 11, while openings 12 are provided in the spines 6 in which the high end $H_1$ of the cams 8 can snugly fit when in the closed position, as shown in FIG. 2. From the closed position as shown in FIG. 2, the stem 2 can be rotated in the direction C around the longitudinal axis A, such that the cams 8 are moved at least partly out of the openings 12, until the low end $H_0$ of the cams 8 abuts against the spines 6, thus limiting the extent of rotational movement in the direction C. In the thus reached open position, as shown in FIG. 3, a blocking means, for example a pin 13 can be inserted into the casing 5, such that rotation back into the direction of the closed position as shown in FIG. 2 is prevented. Such locking can obviously be reached in a number of different ways.

The casing 5 has a substantially oval-shaped outer contour 14, such that when inserted into a hole 15 in a bone, for example a femur, rotation of the casing 5 within this hole 15 is prevented. Within the casing, open spaces 16 are provided, enclosed by the two adjacent bridges 7, the stem 2, especially the cams 8 and the casings 5 on opposite sides. The spaces are slightly C-shaped with increasing depth between the stem 2, at least the cams 8 and the outer contour 14. When the compacting means 3 are in the closed position, as shown in FIG. 2, the volume $V_0$ of each space 16 is relatively large, whereas when rotated into the open position, as shown in FIG. 3, the volume $V_1$ of the spaces 16 is substantially smaller, due to the entering of the higher parts of the cams 8 into said spaces 16. Preferably, the sizes of the cams 8 and stem 2 and the outer contour 14 are chosen such that, in the open position, the outer surface of the cams 8 lies adjacent the outer contour 14.

As schematically shown in FIG. 4 and FIG. 5, on the outside of the stem 2 and/or the contacting means 4, especially on the cams 8, within the spaces 16 and/or on the casing 5 a mass 17 comprising granular material 18 is provided, which granular material is bio-compatible and substantially porous, such that bone and tissue can grow into the mass 17, especially into the granular material 18. Preferably the granular material, which may be sponge-like, is obtained by chemical reaction with titanium tetrachloride. As shown in FIG. 5, the mass 17 can, along the longitudinal direction of the stem 2, have different densities and/or composition. In FIG. 5 for example, the areas between the cams 8 are provided with a mass 17A having a higher density of granular material 18, which granular material may have a hardness which is for example higher than the hardness of the granular material of the mass 17B along the further extent of the prosthesis 4. The mass 17 is preferably provided on the prosthesis 3, for example by using collagen or a different bio-compatible material which will keep the granular material in a closed mass 17, especially glue like material. Alternatively, the mass 17 may be enclosed in a film like material, netting, outer casing or the like, which will be designed such that bone and tissue can grow through into and from the mass 17 once inserted into a hole 15 in the bone 20. In FIG. 5 a hip prosthesis is shown comprising a neck 21 with ball joint 22, only by way of example.

A prosthesis according to the present invention can be used as follows.

A hole 15 is provided in a bone, for example a femur, for example slightly tapered as shown in FIG. 5, having such dimensions that the prosthesis with the mass 17 surrounding can fit relatively closely into the hole 15 with the compacting means 4 in the closed position as shown in FIG. 2. Once the prosthesis is inserted at least almost fully into the hole 15, the casing 5 is prevented from rotation around the longitudinal axis A, preferably due to its shape, after which the stem 2 with the neck 21 and ball joint 22 are rotated around the longitudinal axis A in the direction C, into the open position as shown in FIG. 3 and FIG. 4, thereby forcing the mass 17 at least partly out of the spaces 16 and against the inner wall 23 of the hole 15, thereby compacting the granular material in a suitable manner. The forces exerted on the granular material and on the inner wall 13 are thereby such that bone resorption is at least substantially and preferably totally prevented, while optimal growth conditions are obtained. Due to the shape of the cams 8 and the casing 5, as well as the choice of specific granular material within the spaces and around the stem it is at all times possible to obtain the desired compacting of the mass, without the necessity of for example vibration of the mass.

With an assembly and method according to the present invention a prosthesis can be placed, fixated and loaded directly in a simple, efficient and cost effective way, agreeable to the patient and without the necessity of accessory means such as cement or fixating means such as bone screws and the like. The prosthesis can be prepared before introduction into the bone, without the necessity of adding bone or other body tissue to the mass, although it will be clear that nutrition, bone or other body tissue may, if desired, be added to the mass. The mass 17 can be fixed to the assembly 1 prior to introduction into the hole but the mass 17 may also, possibly additionally, be introduced free from the stem 2, compacting means 4 and/or other parts of the assembly 1.

The casing 6 is in the embodiment shown assembled from two parts, such that the stem 2 with the cams 8 can be enclosed therebetween. Obviously other assembly means can be provided or other production techniques can be used for preparing such.

In FIG. 7 an alternative embodiment of an assembly 1 according to the present invention is shown, in which the compacting means 4 are designed for longitudinal movement along the stem 2. The compacting means comprises a ring-shaped element 30, which can be moved along the stem 2, in longitudinal direction A of the stem, between a first position, schematically shown at the right side of FIG. 7, and a second position shown schematically at the left side of FIG. 7. The ring-shaped element 30 comprises a skirt 31 extending downward from a top ring 32, having a decreasing wall thickness in the direction of the free end 33, facing away from this top ring 32. The stem is slightly conical or cylindrical and is provided with a central stem part 34 and a second skirt 35 surrounding a part of the stem part 34, connected to the stem part 34 near the lower end 36 thereof. The second skirt 35 is divided into a number of fingers 38 extending in longitudinal direction adjacent each other, a wedge shaped space 37 enclosed between the inner surface of said fingers 38 and the outer surface of the stem part 34 next to it. The shape and size of the space 37 is such that in the first position (left-hand side of FIG. 7) the skirt 31 extends only partly into the space 37, abutting against at least part of the inner surface of the fingers 38 and the outer surface of the stem part 34. A mass 17 comprising the sponge-like, granular material 18 is provided at least on part of the outer surface 39 of the assembly, especially on the outer surface of the fingers 38 and/or the stem 2. When the prosthesis, at least the stem 2 thereof is introduced into a fitting hole 15 in bone the compacting means 4, that is the ring-shaped element 30 with the skirt 31 is forced down to the second position (right-hand side FIG. 7) forcing the fingers 38 at least partly outward, due to the wedge shape of the fingers 38 and/or space 37. The granular material 18 is thereby forced against the inner wall of the hole 15 and thus compacted. By proper design of especially the fingers and skirts and preferably providing a properly fitting hole, the desired degree of compacting can reproducibly be reached, without the necessity of vibration. A resilient finger 40 is provided on at least one finger or the stem, a compatible opening 41 being provided on the other of stem and finger, such that when the fingers are brought into the second position the resilient finger 40 extends into the opening 41, thereby preventing movement of the fingers 38 back to the first position.

Rotation of the compacting means as shown in FIG. 1-6 may be advantageous since no downward force is needed on the prosthesis. Longitudinal movement for compacting may be advantageous, for example because the prosthesis can be inserted in the right position, without the necessity of rotation of the neck 21 and ball joint 22.

The present invention is by no means limited to the embodiments described or shown in the drawings. Many variants are considered to fall within the scope defined by the claims and the essence of the present invention.

Various combinations of parts of the embodiments shown can be made, for example compacting means which allow both rotational and longitudinal movement for compacting. Similar compacting means can be used for other prostheses, for example for cups which may be press fitted into fitting holes, thereby mechanically compacting a mass comprising granular material. At least part of the outer surface of such cups may be provided with this mass prior to use. The mass can be fixed to the stem and compacting means in various manners, some of them mentioned before. The shape of the compacting means such as cams 8 and fingers 38 may be varied, whereas different shapes may be used in the same compacting means, for example for varying the rate of compacting of the mass 17, especially of the granules 18 therein. It is important that the granules are at least partly compacted, that is, forced in close contact to each other and/or to parts of the assembly and/or to the inner wall of a hole in which the prosthesis is to be fixated by mechanical means.

The invention claimed is:

1. A prosthesis assembly for fixating a prosthesis having a stem for insertion into a hole in bone, the assembly comprising a mechanical compacting device including the stem and a casing surrounding at least a portion of the stem and where the stem is moveable relative to the casing and a mass comprising at least granules of a biocompatible material having a sponge-like structure, wherein the mechanical compacting device includes compacting means for forcing the mass against an inner wall of the hole upon movement of the stem relative to the casing when the assembly is within the hole.

2. An assembly according to claim 1, wherein the compacting means includes openings in the casing and cams within the casing and rotatable relative to the casing and corresponding to the openings and with the cams having an increasing radial height and the mechanical compacting device defining corresponding volumes between each cam, the opening in the casing and the inner wall of the hole, whereby the corresponding volumes receive the mass therein and rotation of a cam reduces a corresponding volume thereby compacting the mass.

3. An assembly according to claim 2, wherein the stem includes the cams disposed thereon.

4. An assembly according to claim 2, wherein the corresponding volumes increase from a first end to a second end of the casing.

5. An assembly according to claim 1, wherein the mass comprises at least granules of two different hardnesses.

6. An assembly according to claim 1, wherein the mass comprises granules of at least two different sizes.

7. An assembly according to claim 1, wherein the compacting device compacts the mass containing granules by rotation of at least the stem relative to the casing.

8. An assembly according to claim 1, wherein the compacting means includes cams disposed on the stem.

9. An assembly according to claim 1, wherein the compacting means are designed to provide, during use, a mass compacting rate near an opening of a hole in which the prosthesis is fixed which is higher than the compacting rate of the prosthesis at a distance from said opening of the hole, such that bending of the prosthesis below said opening of the hole is possible for obtaining micro motion for inducing bone growth into said granules.

10. An assembly according to claim 1, wherein said granules are made of titanium or titanium blends.

11. An assembly according to claim 10, wherein the granules are chemically treated for obtaining a desired porosity.

12. An assembly according to claim 1, wherein the body tissue is bone of a mammal.

13. An assembly according to claim 1, wherein the granules are chemically treated for obtaining a desired porosity.

14. An assembly according to claim 1, wherein the compacting means includes openings in the casing and a plurality of cams within the casing and rotatable relative to the casing and corresponding to the openings and with the plurality of cams having an increasing radial height and the mechanical compacting device defining corresponding volumes between each cam, the opening in the casing and the inner wall of the hole, whereby the corresponding volumes receive the mass therein and rotation of a cam reduces a corresponding volume thereby compacting the mass.

15. A method for preparation of a prosthesis having a stem for fixation in a hole in a bone, comprising providing the prosthesis with compacting means for forcing a mass against an inner wall of the hole in the bone which compacting means encloses at least one space, into which at least one space the mass is introduced, said mass comprising at least granules of a biocompatible material having a sponge-like structure and into which said prosthesis is to be positioned, said compacting means including the stem, cams and a casing surrounding at least a portion of the stem and having openings and where the stem and the cams are moveable relative to the casing.

16. A method according to claim 15, wherein said mass is prepared comprising at least two types of granules, different in at least hardness or size.

17. A method according to claim 15, wherein the opening is a bore in bone.

18. A method according to claim 15, wherein the prosthesis further comprises fixation means that includes a stem.

19. Assembly for fixating a prosthesis in a hole in bone, comprising a mechanical compacting device and a mass comprising at least granules of a biocompatible material, the mechanical compacting device including compacting means for forcing the mass against an inner wall of the hole upon relative movement of at least a first part of the compacting means relative to a second part thereof, such that the volume of at least one space between at least part of an outer surface of the compacting means and the adjacent inner surface of said hole is reduced, wherein the granules have a sponge like structure, such that bone and tissue can grow into said mass and wherein the compacting device is at least partly integrated with the prosthesis.

20. Assembly according to claim 19, wherein the mass is provided on an outer surface of the assembly and the mechanical compacting device is designed for reducing said volume in a direction substantially perpendicular to said outer surface.

21. Assembly according to claim 19, wherein the compacting device is designed for compacting the mass containing granules by rotation of at least said first part relative to said second part.

22. Assembly according to claim 21, wherein said first part comprises ribs or cams which in a first position are enclosed within the second part to a first extend and in a second position are enclosed in said second part to a lesser extent, such that during use by rotation of the first part relative to said second part from the first position to the second position said volume of said space is reduced, thereby compacting the mass.

23. Assembly according to claim 19, wherein said first part comprises ribs or cams and the second part comprises a skirt which in a first position is enclosed within the first part to a first extent and in a second position is enclosed in said second part to a further extent, such that during use by translation of the second part relative to said first part from the first position to the second position said volume of said space is reduced, thereby compacting the mass.

24. Assembly according to claim 19, wherein the compacting means include cams positioned longitudinally along the compacting device and provide varying degrees of compacting.

25. Assembly according to claim 19, wherein said device comprises a first end and a second end, spaced longitudinally, wherein the compacting means provide, during use, decreasing compacting in the direction of the second end.

26. Assembly according to claim 19, wherein the mass comprises at least granules of two different hardness.

27. Assembly according to claim 19, wherein the mass comprises granules of at least two different sizes.

28. Assembly according to claim 19, wherein said mass comprises granules obtained by a reaction with titanium tetrachloride.

29. Assembly according to claim 19, wherein the compacting means are designed to provide, during use, a mass compacting rate near an opening of a hole in which the prosthesis is fixed which is higher than the compacting rate of the prosthesis at a distance from said opening of the hole, such that bending of the prosthesis below said opening of the hole is possible for obtaining micro motion for inducing bone growth into said granules.

30. Method for preparation of a prosthesis for fixation in an opening such as a bore in bone, comprising providing the prosthesis with compacting means for forcing a mass against an inner wall of the bore, characterized in that said compacting means enclose at least one space, into which at least one space the mass is introduced, said mass comprising at least granules of a biocompatible material having a sponge like structure and into which said prosthesis is to be positioned, said compacting means being arranged for compacting said mass around at least part of fixation means of said prosthesis and wherein said compacting means is at least partly integrated with the prosthesis.

31. Method according to claim 30, wherein said mass is prepared comprising a mixture at least two types of granules, different in at least hardness or size.

32. Method according to claim 30, wherein said mass is prepared comprising at least two types of granules, different in at least hardness.

33. A method according to claim 30, wherein the opening is a bore in bone.

34. A prosthesis assembly for fixating a prosthesis having a stem for insertion into a hole in bone, the assembly comprising a mechanical compacting device including the stem and a casing surrounding at least a portion of the stem and where the stem is moveable relative to the casing and a mass comprising at least granules of a biocompatible material, wherein the mechanical compacting device includes compacting means for forcing the mass against an inner wall of the hole upon movement of the stem relative to the casing when the assembly is within the hole.

35. An assembly according to claim 34, wherein the compacting means includes openings in the casing and cams within the casing and rotatable relative to the casing and corresponding to the openings and with the cams having an increasing radial height and the mechanical compacting device defining corresponding volumes between each cam, the opening in the casing and the inner wall of the hole, whereby the corresponding volumes receive the mass therein and rotation of a cam reduces a corresponding volume thereby compacting the mass.

* * * * *